(12) United States Patent
Oh et al.

(10) Patent No.: US 7,802,589 B2
(45) Date of Patent: Sep. 28, 2010

(54) MULTIRATE TUBING FLOW CONTROL VALVE

(75) Inventors: Seik Oh, Laguna Hills, CA (US); James B. Winje, Franklin Park, IL (US); Mark E. Williamson, Wonder Lake, IL (US)

(73) Assignees: Baxter International Inc., Deerfield, IL (US); Baxter Healthcare S.A., Glattpark (CH)

( * ) Notice: Subject to any disclaimer, the term of this patent is extended or adjusted under 35 U.S.C. 154(b) by 0 days.

(21) Appl. No.: 12/715,827

(22) Filed: Mar. 2, 2010

(65) Prior Publication Data

US 2010/0154909 A1   Jun. 24, 2010

Related U.S. Application Data

(63) Continuation of application No. 11/458,903, filed on Jul. 20, 2006, now Pat. No. 7,690,396.

(51) Int. Cl.
*F16K 5/10* (2006.01)

(52) U.S. Cl. ............... 137/625.3; 137/625.32; 251/209

(58) Field of Classification Search ............ 137/599.04, 137/599.05, 625.3, 625.32; 251/209; 604/32, 604/246, 248
See application file for complete search history.

(56) References Cited

U.S. PATENT DOCUMENTS

| | | | |
|---|---|---|---|
| 944,026 A * | 12/1909 | Fowden ................ | 137/556.3 |
| 2,998,023 A * | 8/1961 | Campbell et al. ...... | 137/599.05 |
| 3,072,146 A * | 1/1963 | Gizeski ................ | 137/552 |
| 3,276,472 A | 10/1966 | Jinkens et al. | |
| 3,325,143 A * | 6/1967 | Phillips ................ | 251/311 |
| 3,678,960 A | 7/1972 | Leibinsohn | |
| 3,774,604 A | 11/1973 | Danielsson | |
| 3,834,372 A | 9/1974 | Turney | |
| 4,210,178 A | 7/1980 | Morse et al. | |
| 4,375,813 A | 3/1983 | Hessel | |
| 4,566,480 A | 1/1986 | Parham | |
| 4,593,717 A | 6/1986 | Levasseur | |
| 4,694,856 A | 9/1987 | Leibinsohn | |
| 4,738,283 A | 4/1988 | Shirai et al. | |
| 4,802,506 A * | 2/1989 | Aslanian .............. | 137/556 |
| 4,967,797 A | 11/1990 | Manska | |
| 5,009,251 A | 4/1991 | Pike et al. | |
| 5,019,054 A * | 5/1991 | Clement et al. ........ | 604/248 |
| 5,144,972 A | 9/1992 | Dryden | |
| 5,427,145 A | 6/1995 | Grabenkort | |

(Continued)

FOREIGN PATENT DOCUMENTS

DE   4323613   1/1995

(Continued)

OTHER PUBLICATIONS

International Search Report for International Application No. PCT/US2007/072104 dated Jan. 3, 2008.

*Primary Examiner*—John Fox
(74) *Attorney, Agent, or Firm*—K&L Gates LLP

(57) ABSTRACT

A flow control valve includes a stem extending into an interior bore defined by a wall of a flow control member of the valve, the stem and the wall defining therebetween a cylindrical space allowing fluid communication between apertures formed in differing planes of the flow control member.

20 Claims, 6 Drawing Sheets

U.S. PATENT DOCUMENTS

| | | |
|---|---|---|
| 5,439,452 A | 8/1995 | McCarty |
| 5,443,453 A | 8/1995 | Walker et al. |
| 5,466,228 A | 11/1995 | Evans |
| 5,499,968 A | 3/1996 | Milijasevic et al. |
| 5,817,068 A | 10/1998 | Urretia |
| 5,927,326 A | 7/1999 | Heijima et al. |
| 6,273,133 B1 | 8/2001 | Williamson et al. |
| 2005/0038387 A1 | 2/2005 | Kriesel et al. |
| 2005/0277884 A1 | 12/2005 | Kriesel et al. |

FOREIGN PATENT DOCUMENTS

| | | |
|---|---|---|
| EP | 0 800 837 | 10/1997 |
| JP | 9-225028 | 9/1997 |
| WO | 03/039646 | 5/2003 |
| WO | 2004/026373 | 4/2004 |
| WO | 2004/039446 | 5/2004 |

\* cited by examiner

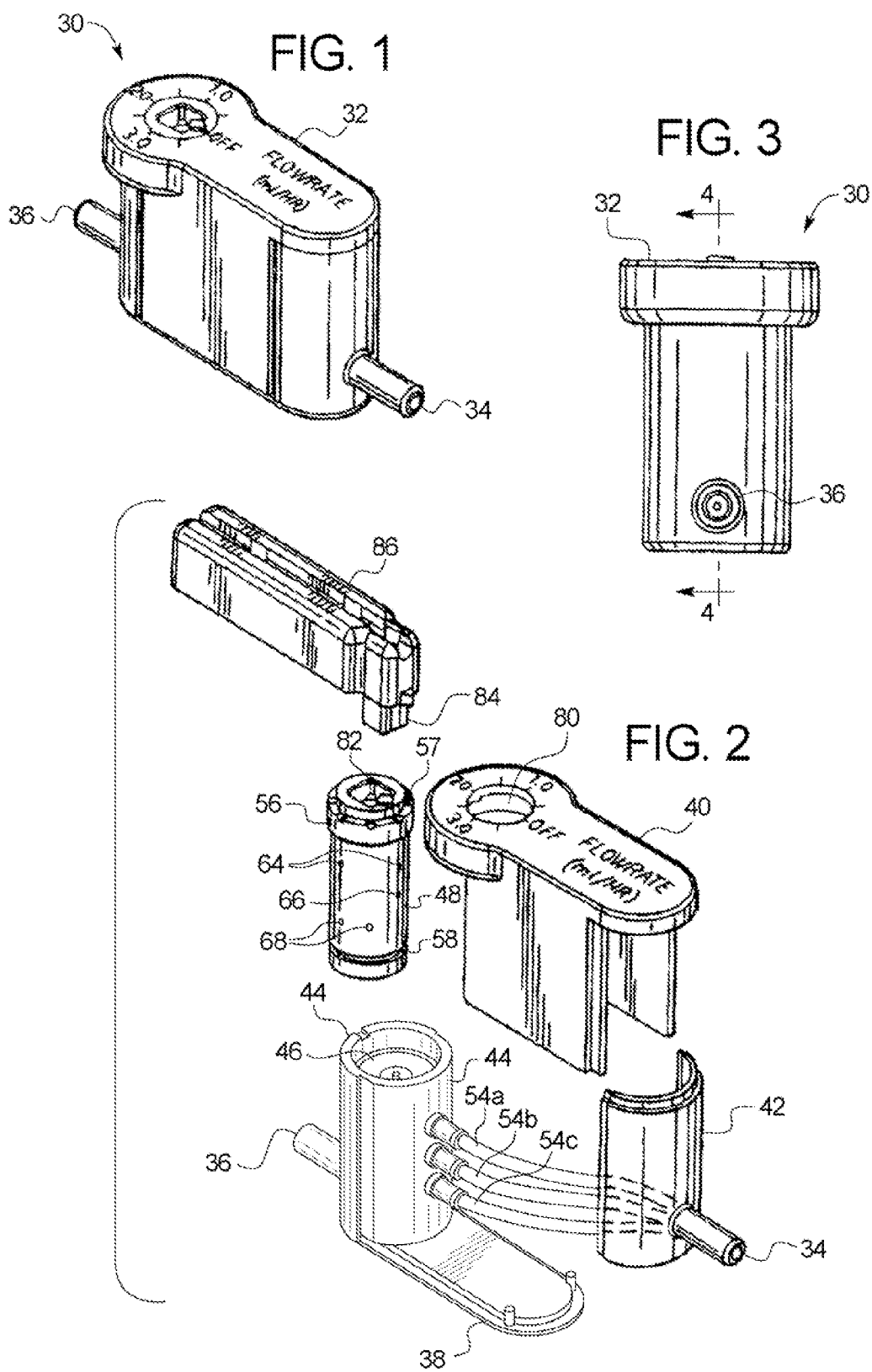

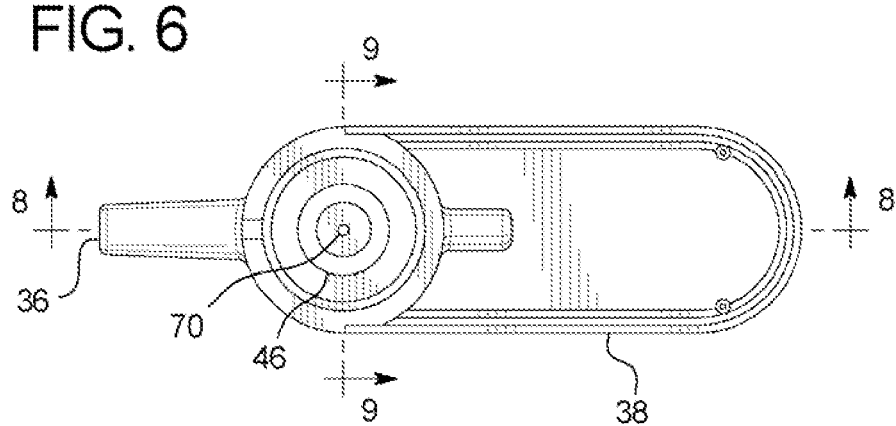
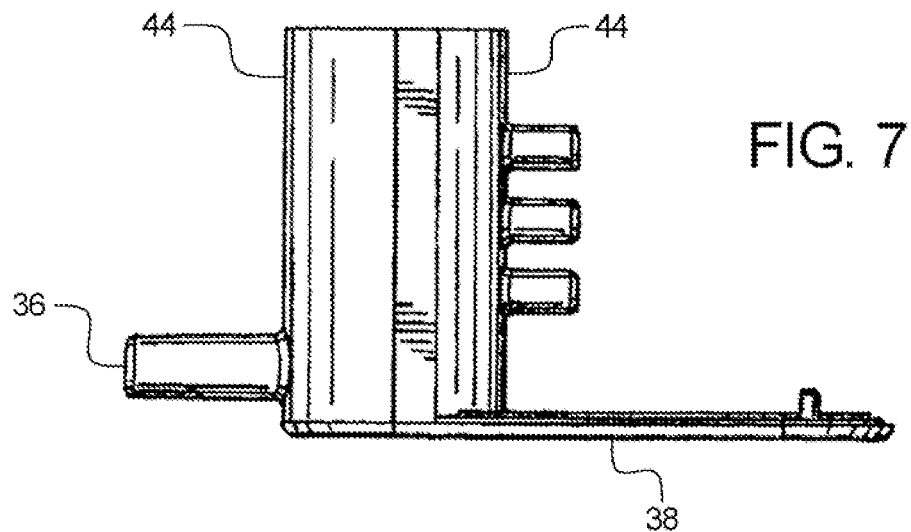
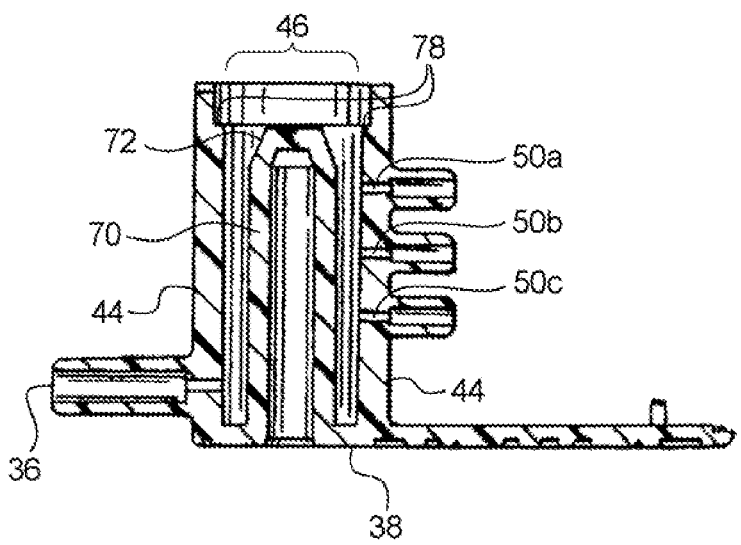
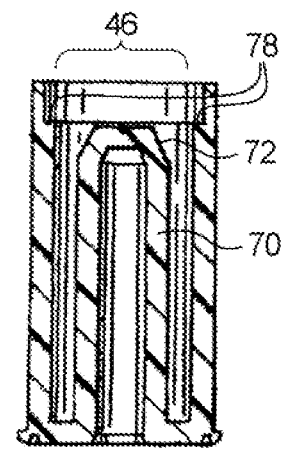

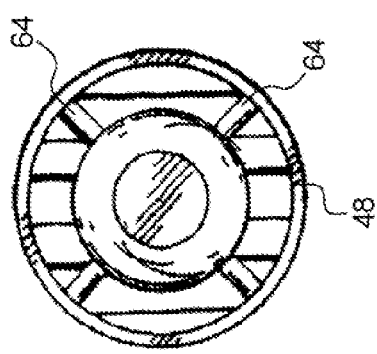
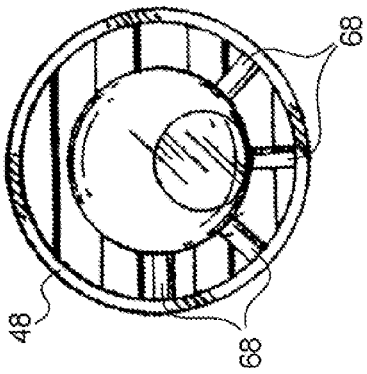
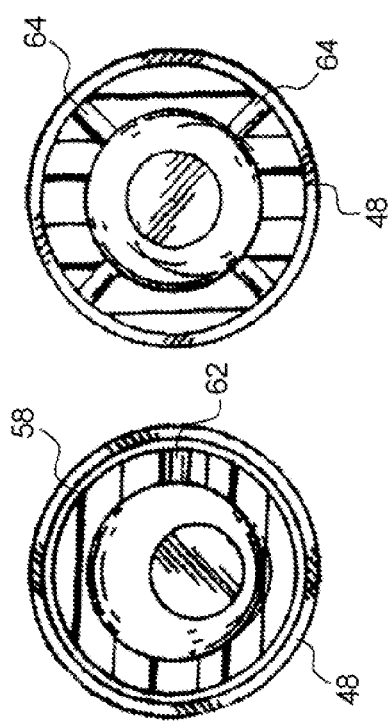
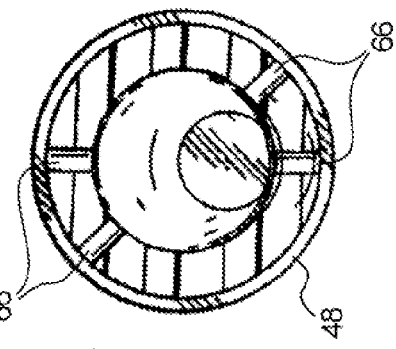
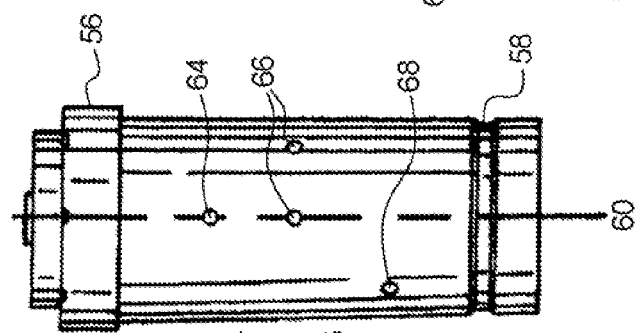
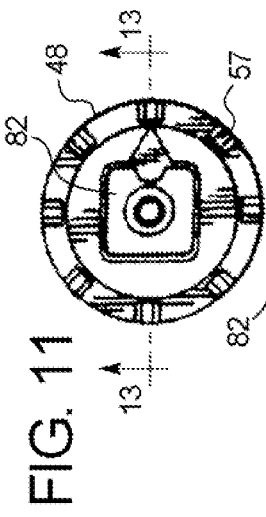
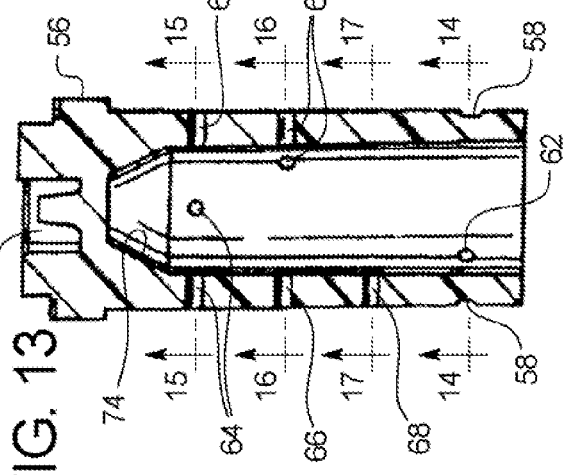
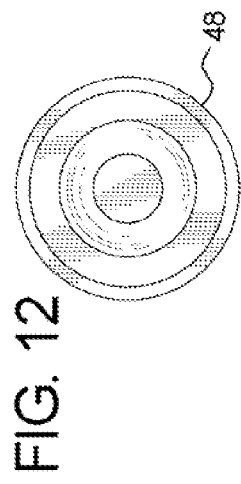

MULTIRATE TUBING FLOW CONTROL VALVE

PRIORITY CLAIM

This application is a continuation application and claims priority to and the benefit of U.S. patent application Ser. No. 11/458,903, entitled Multirate Tubing Flow Restrictor, filed Jul. 20, 2006.

BACKGROUND

The present invention generally relates to a flow control valve for medical liquid, and more particularly to a multi-rate flow control device for dispensing a medical fluid at a selected one of a plurality of discrete flow rates.

In the delivery of medical liquids, such as medication, drugs, chemotherapeutic agents, intravenous solutions or the like, it is known to use a flow control valve that permits the user to select a particular flow rate from a range of discrete flow rates. One such flow control valve, which uses glass capillary structures to control the flow rate, is described in U.S. Pat. No. 6,273,133 entitled "Fluid Flow Rate Switching Device." The device shown there has two internal passageways, each with a glass capillary structure that limits flow through the passageway. A valve member directs fluid flow through either or both of the passageways to provide several different flow rates through the flow control device. While this device works satisfactorily, the use of glass capillary structures can add to the cost and there is a desire to have flow control devices with a greater selection of available flow rates. Although this is but one example, there continues to be a need for medical fluid flow control valves that address one or more of the drawbacks found in prior valves.

SUMMARY

The present invention is embodied in a novel flow control device or valve that is relatively easily and inexpensively manufactured and provides a variety of flow rates for doctor or user selection. In one aspect of the present invention, a flow control valve for dispensing medical liquid is provided. The flow control valve includes a housing comprising an inlet, an outlet, and a flow path therebetween. A plurality of flow restrictors in the flow path define a plurality of flow streams of differing flow rates. A flow control member is disposed in the flow path and has at least one aperture disposed in a first plane and at least one aperture disposed in a second plane which is spaced apart from the first plane. The flow control member is movable relative to the housing between a first position and at least one second position. In the first position, one of the at least one apertures in the first plane is in communication with at least one of the flow streams to define a first flow rate through the valve. In the second position, one of the at least one apertures in the second plane is in communication with a different one of the flow streams to define a second flow rate through the valve different from the first flow rate.

In a second aspect of the present invention, a flow control valve for dispensing medical liquid is also provided. The flow control valve includes a housing comprising an inlet, an outlet, and a flow path therebetween. A plurality of flow regulators disposed in the flow path define a plurality of differing flow rates. A first of the plurality of flow regulators is defined by a tube of a first selected size. A second of the plurality of flow regulators is defined by a tube of a second selected size which is different from the size of the first flow regulator. A flow control member disposed in the flow path has at least one discrete aperture at each of a first and second spaced apart locations. The flow control member is movable relative to the housing between a first position and a second position and defines an annular gap which is in communication with the outlet. In the first position, one aperture in the first location is in communication with one of the flow regulators to define a first flow rate through the valve. In the second position, one aperture in the second location is in communication with a different one of the flow regulators to define a second flow rate through the valve which is different from the first flow rate.

The flow control member of the valve in this aspect of the invention is rotatable between at least a first and second position. In the first position, one of the plurality of apertures in the first plane is in communication with the first opening in the annual wall to define a first flow rate through the valve. In the second position, one of the plurality of apertures in the second plane is in communication with the second opening in the annual wall to define a second flow rate through the valve that is different from the first flow rate.

In a fourth aspect of the invention, a flow control valve for dispensing medical liquid is provided. The flow control valve includes a housing comprising an inlet, an outlet, and a flow path therebetween. The housing includes an annular wall defining an interior bore and first and second axially spaced-apart openings extending through the annular wall. Within the interior bore, a flow control member is rotatably disposed and has a plurality of discrete apertures in each of a first and second plane.

The flow control member in this fourth aspect of the invention also defines a portion of a passageway that extends in a direction generally normal to at least one of the first and second planes and communicates with the discrete apertures and one of the inlet and outlet regardless of the position of the flow control member.

Additional features and advantages are described herein, and will be apparent from the following Detailed Description and the figures.

BRIEF DESCRIPTION OF THE FIGURES

FIG. 1 is a perspective view of one embodiment of a flow control device employing the present invention;

FIG. 2 an exploded perspective view of the view of the flow control device of FIG. 1.

FIG. 3 is an end view of the flow control device of FIG. 1.

FIG. 6 is a top view of the base of the flow control device of FIG. 2.

FIG. 7 is a side view of the base of the flow control device illustrated in FIG. 6.

FIG. 8 is a cross-sectional view of the base of the flow control device of FIG. 6, taken through line 8-8.

FIG. 9 is a cross-sectional, end view of the base of the flow control device of FIG. 6, taken through line 9-9.

FIG. 10 is a side view of the flow control member of FIG. 1.

FIG. 11 is a top view of the flow control member of FIG. 10.

FIG. 12 is a bottom, plan view of the flow control member of FIG. 10.

FIG. 13 is a cross-sectional view of the flow control member of FIG. 11 taken along line 13-13.

FIG. 14 is a cross-sectional view of the flow control member of FIG. 13 taken along line 14-14.

FIG. 15 is a cross-sectional view of the flow control member of FIG. 13 taken along line 15-15.

FIG. 16 is a cross-sectional view of the flow control member of FIG. 13 taken along line 16-16.

FIG. 17 is a cross-sectional view of the flow control member of FIG. 13 taken along line 17-17.

DETAILED DESCRIPTION

Figure 4:
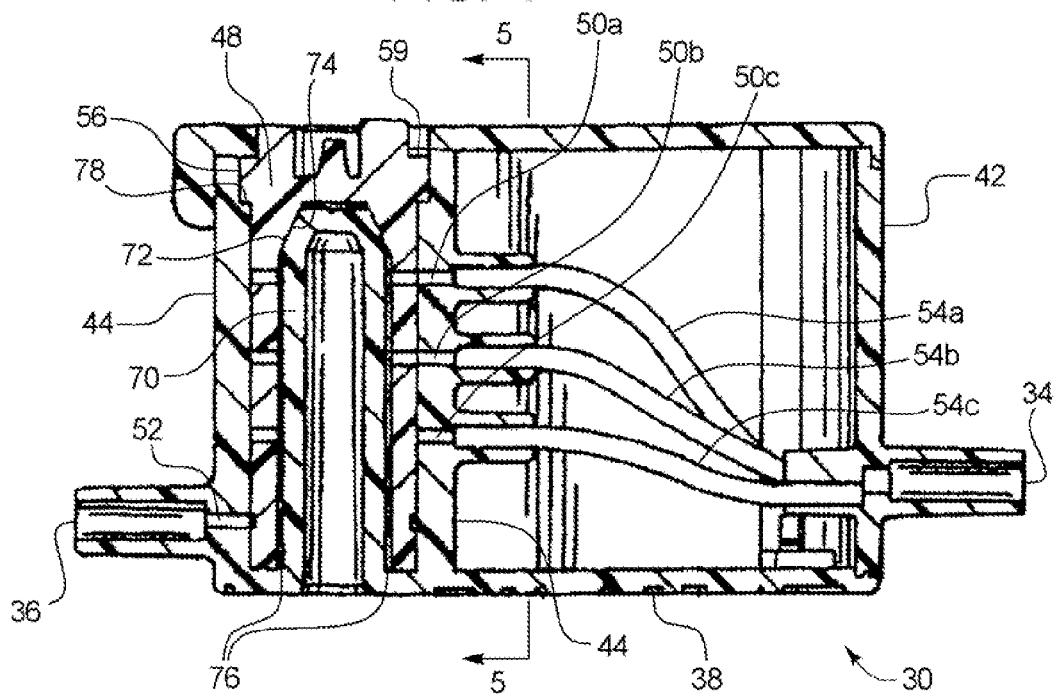
FIG. 4 is a cross-sectional view of the flow control device of FIG. 1 taken through line 4-4 of FIG. 3.
Figure 4A:
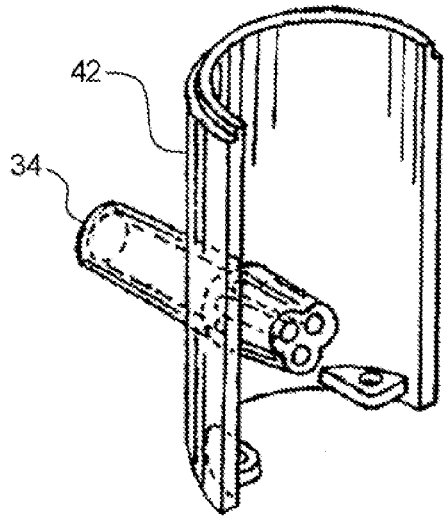
FIG. 4A is a broken away, perspective of a portion of FIG. 1, showing the inlet diverging into three separate flow restrictors or tubes.

Referring to FIG. 1, the present invention is generally embodied in a flow control device, generally at 30. The flow control device 30 includes a housing 32 having an inlet 34 and an outlet 36, and a flow path defined between the inlet and outlet. The embodiment shown in the drawings is for purpose of illustration only, and it should be understood that the form and features of the flow control device of the present invention may vary according to the desired application or intended function. The scope of this invention is as defined in the claims now or hereafter submitted and except to the extent included in such claims, is not limited to any specific form, feature or function described herein.

As shown in FIG. 2, in exploded view, the illustrated flow control device 30 includes a base or bottom portion 38, a top and side portion 40 and an end portion 42. The housing is preferably made of rigid molded plastic, although other suitable materials may also be used.

Figure 5:
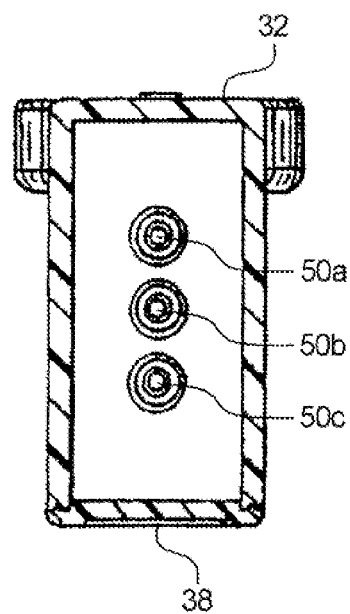
FIG. 5 is a cross-sectional end view of the flow control device of FIG. 4 taken through line 5-5.
Figure 18:
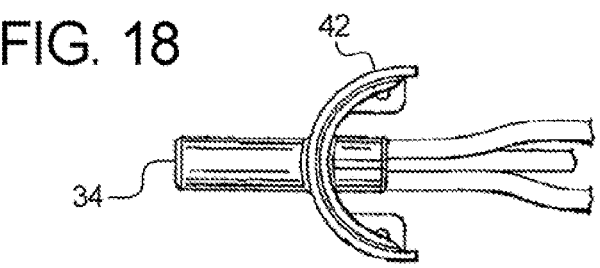
FIG. 18 is a top view of portion of the housing of the flow control device of FIG. 1.
Figure 19:
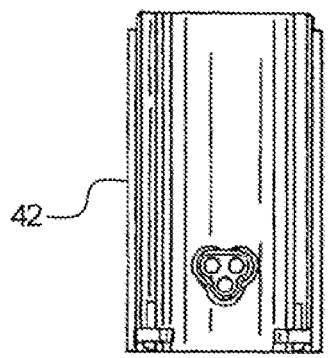
FIG. 19 is an interior view of the inlet end of the flow control device of FIG. 8, taken along line 19-19, with the tubes removed.
Figure 20:
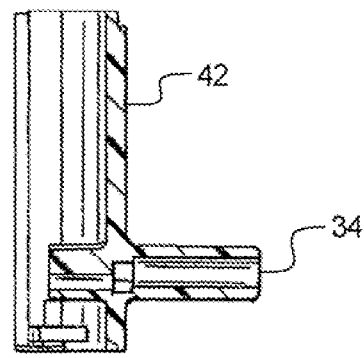
FIG. 20 is a cross-sectional view of FIG. 19 taken through line 20-20.
Figure 22:
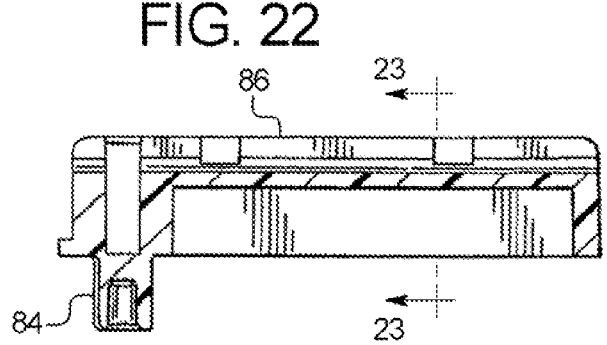
FIG. 22 is a side, cross-sectional view of the tool of FIG. 21 taken along line 22-22.
Figure 23:
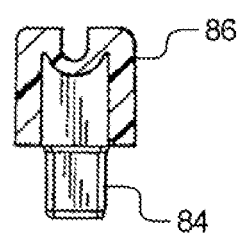
FIG. 23 is a cross-sectional, end view of the tool of FIG. 22 taken along line 23-23.
Figure 21:
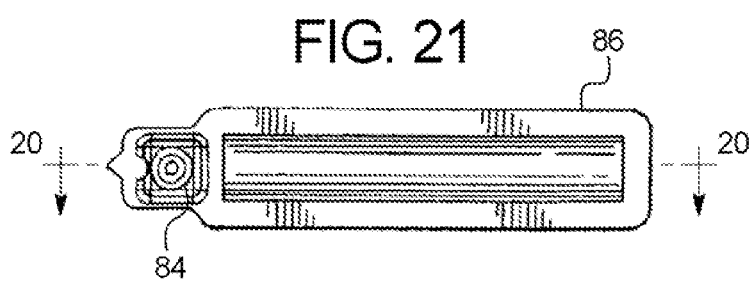
FIG. 21 is a top view of a tool used to adjust the intended position of the flow control member of the flow control device of FIG. 1.

The flow control device of the present invention preferably includes a movable flow control member associated with the housing to control flow therethrough. In the illustrated embodiment, the base 38 has an upstanding, generally cylindrical or annular wall 44, which forms a generally cylindrical interior bore 46 for receiving a rotating flow control member or valve element 48 that serves, in part, to control the flow rate of fluid through the housing. As best seen in FIGS. 2, 4 and 5, a plurality of axially spaced-apart apertures or ports 50a, 50b and 50c extend through the annular wall 44. Outlet 36 also includes an aperture or port 52 extending through wall 44.

A length of plastic tubing 54a, 54b, 54c of selected size extends between each aperture 50a, 50b and 50c and the inlet 34. Each tube is of a different size, diameter and/or length, to act as a flow restrictor or a flow setter to create a fluid flow stream having a selected flow rate different than the flow rate in the other tubes. For example, under the normal pressure exhibited by an elastomeric pump in the flow administration of IV solution to a patient, tube 54a is sized to provide a flow stream with a flow rate of 1.0 ml/hr between the inlet port and aperture 50a, tube 54b is sized to provide a flow stream with a flow rate of 2.0 ml/hr between the inlet port and aperture 50b, and tube 54c is sized to provide a flow stream with a flow rate of 4.0 ml/hr between the inlet port and aperture 50c. In a preferred embodiment the 1.0 ml/hr tubing has an ID of 0.0021 inches and a length of 3.67 inches, the 2.0 ml/hr tubing has an ID of 0.0031 inches and a length of 3.65 inches and the 4.0 ml/hr tubing has an ID of 0.0036 inches and a length of 3.20 inches. It should be understood that tubings having different ID's and lengths may be employed to get the illustrated flow rates or other desired flow rates. It is apparent that use of a tubing having a smaller diameter and/or longer length would yield a tubing which provides a flow stream of 0.5 ml/hr.

Although illustrated with three different tubes, additional or fewer tubes may also be used. Also, structures other than tubing may be employed to function as flow restrictors or flow setters, including orifices, molded passageways, and the like. Tubing, however, is relatively easy to extrude and bond to the respective ports or apertures, and thus serves to minimize manufacturing cost.

In accordance with the present invention, a plurality of selected discrete flow rates may be provided through the flow control device by selectively allowing flow from one or more of the flow restrictor tubings to pass through the housing. In the illustrated device, this flow control is provided by the flow control or valve member 48, which is best seen in FIGS. 10-17, in cooperation with the features described above.

As shown in FIGS. 10 and 13, the flow control member is generally hollow and cylindrical, and made of molded plastic or other suitable material. The flow control member has an exterior surface of generally uniform diameter except for an enlarged annular collar 56 at one end and an annular groove or channel 58 at the other end. "Uniform diameter" is intended to include a surface having a slight taper, such as a molding draft angle or taper, on either or both of the control member 48 and inner surface of bore 46. The illustrated flow control member has one or more apertures in each of a plurality of axially spaced apart regions or planes. In the illustrated valve member, there are four such regions or planes, generally shown in FIGS. 14-17, although the number can vary. At least one of the planes, however, includes a plurality of apertures.

More specifically. FIG. 14 is a cross-sectional view taken along line 14-14 of FIG. 13, which is generally perpendicular to the axis 60 of the flow control member 48. For purposes of this description this will be referred to as region or plane 14-14. As evident from FIGS. 13 and 14, plane 14-14 extends through the annular groove 58, and has a single aperture 62. As will be described in more detail later, when assembled in the housing, annular groove 58 is in registration (fluid communication) with outlet port aperture 52 regardless of the orientation of the flow control member 48.

Using the same terminology, plane 15-15 is located at the other end of the flow control member 48. As seen in FIG. 15, this region or plane contains four apertures 64, circumferentially spaced apart 90°, and are oriented (in a clockwise direction from the 9 o'clock position) at the 45°, 135°, 225° and 315° positions. As best seen in FIG. 16, plane or region 16-16 of FIG. 13 also includes four apertures 66, which are oriented (in a clockwise direction from the 9 o'clock position), at the 45°, 90°, 225° and 270° positions. Plane 17-17 of FIG. 13 is located between planes 14-14 and 16-16. As shown in FIG.

17, this plane or region includes four apertures 68, which are oriented (in a clockwise direction from the 9 o'clock position) at the 0°, 225°, 270° and 315° positions.

As noted earlier, and as best seen in FIG. 4, the flow control member 48 is rotatably received within the bore 46 defined in the base portion 38 of the housing 32. The flow control member 48 is sized so that it is in relatively liquid tight interference fit with the inner surface of bore 46. More specifically, the fit between the outside surface of the flow control member 48 and inner surface of bore 46 should preferably be sufficiently liquid tight so that there is no substantial fluid flow or leakage between the surfaces, either between apertures 50a-50c or between apertures 50a-50c and the outlet aperture 62. The fit however cannot be so light that the flow control member 48 may not be rotated with the typical force which may be applied to the member. Thus a leakage tight fit is provided without the use of O-rings or other typical rotational seals which would increase the complexity of manufacture and cost.

When fully inserted into the bore, the annular groove 58 of the flow control member is aligned with outlet port aperture 52, and planes 15-15, 16-16 and 17-17 are each aligned, respectively, with one of the apertures 50a, 50b and 50c through the cylindrical wall 44. By rotating flow control member, one or more of the apertures 64, 66 and 68 in each plane or region can be brought into registration or alignment (flow communication) with any of the respective apertures 50a, 50b, 50c, through which the flow stream passes from one of the flow restrictor tubings 54a, 54b and 54c.

To stabilize the flow control member and aid assembly, the housing base 38 includes a center cylindrical support member 70 within bore 46. When assembled, the support member extends through the center of the flow control member 48. The upper end of the support member 70 is tapered at 72 to engage a matching internal taper 74 in the flow control member to assist in assembly and centering alignment.

The outside diameter of the support member 70 is smaller than the inside diameter of flow control member 48 and, as a result, an annular flow path 76 in the form of an annular region or gap is defined between them. In the illustrated orientation, this flow path 76 extends axially or vertically between the support member 70 and flow control member 48 through each of the horizontal regions or planes 14-14 through 17-17. Thus, fluid flowing through any of the apertures in planes 15-15 through 17-17 is combined in and conducted through the flow path 76 defined between support member and flow control member and directed to aperture 62 (in plane 14-14).

The outer diameter of the support member 70 and inside diameter of the control member 48 are preferably sized to provide several desired benefits. One such benefit is to define a flow path which does not provide an appreciable resistance to flow but also define a volume which is low to minimize priming and residual volume. Because of the typical low flow rates, the larger the volume the longer the time to prime, and the larger the volume of fluid that is not dispensed to the patient. A second benefit is that the thickness of the tubular walls of the control member 48 may be controlled such that it may be molded with tight tolerances to provide the fluid tight interference fit with the bore 46 as described above. It has been found that if the thickness is too great, it is harder to maintain the tolerance of the outer diameter of the control member 48 to provide the desired interference fit.

Another benefit of the flow control member 48 is the placement of an aperture 62 that communicates in all rotational positions, via annular groove 58, with outlet port aperture 52. Thus in a preferred embodiment regardless of the orientation of the flow control member 48 to provide a desired communication with none, one or more of the apertures 50, the outlet port aperture 52 is always in communication with the annular flow path 76.

As best seen in FIGS. 2 and 4, when assembled, the upper annular collar 56 of the flow control member is captured between an internal shoulder 78 of bore 46 and the top wall of the housing. To rotate the flow control member to selected flow positions, the upper end of the flow control member is accessible through an opening 80 in the upper wall of the housing (see FIG. 2). The upper end of the flow control member defines a recess 82 of selected shape, such as square, triangular or other cross-sectional to interfit with a complementary—shaped end 84 of tool 86 to allow the clinician or health care worker to rotate the flow control member. Preferably the recess 82 is located recessed or below the upper wall of the housing to prevent inadvertent or unauthorized turning of the flow control member by one who does not possess the tool 86.

Referring in particular to FIGS. 4 and 10, the flow device 30 (FIG. 1) includes means for imparting a tactile sensation to the setting of the desired flow rate. In particular the upper annular collar 56 includes a series of detents 57 radially spaced about the upper surface of the collar. These detents 57 register with a downwardly projecting bump 59 on the top portion 40 to preferably impart a tactile and audible indication that the flow control member 48 is properly oriented to provide the desired flow rate. The flow rates may also be depicted on the top portion 40 as is illustrated in FIG. 2.

Figure 24A:
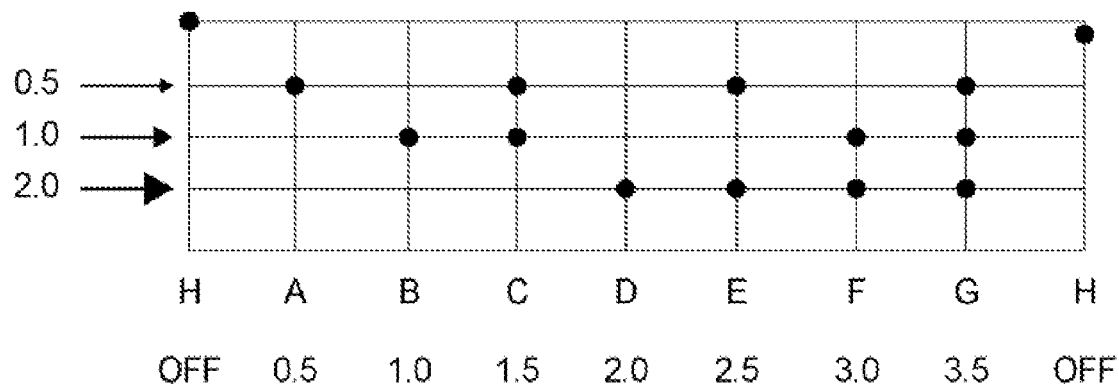
FIG. 24A is a diagram which pictorially illustrates an expanded view of a generally cylindrical side wall of the flow control member identifying the component flow streams that are in communication with the outlet at different positions of the flow control member in the flow control device of FIG. 1.
Figure 24B:
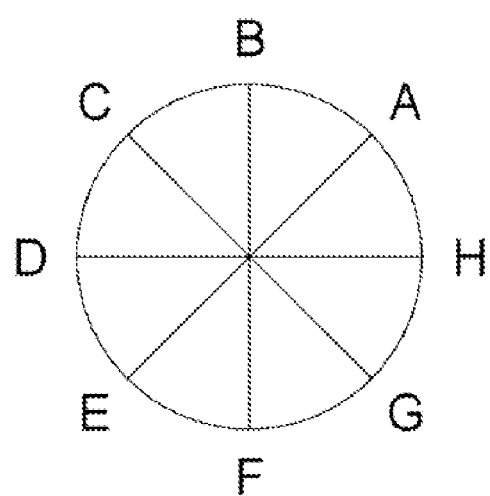
FIG. 24B is a top view of the flow control member with superimposed indicator lines showing each of the different rotational positions which the flow control member in the flow control device of FIG. 1, corresponding to the arrangement of the apertures for the flow streams shown in FIG. 24A.

By way or example when the flow rates provided by the flow restrictor tubing 54a is 0.5 ml/hr: by flow restrictor tubing 54b is 1.0 ml/hr and by flow restrictor tubing 54c is 2.0 ml/hr and as depicted in FIGS. 24A and 24B, the illustrated flow control device provides seven specific discrete flow rates, in addition to an "off" position. FIG. 24B shows eight different rotational positions of the flow control member, each designated by a letter A-H. The graph or chart in FIG. 24A diagrammatically shows which apertures in the flow control member are in communication with which of the flow restrictor tubing in each of the rotational positions. With these example provided restrictor 110W tubing, in position A, one of the apertures 64 in plane 15-15 communicates with aperture 50a and the flow restrictor tubing 54a, thereby providing a flow rate of 0.5 ml/hr. No aperture in planes 16-16 or 17-17 communicates with the other flow restrictor tubing. The resultant flow rate through the valve is therefore 0.5 ml/hr.

In position B of FIG. 24B, one of the apertures in plane or region 16-16 is in alignment or registration with aperture 50b), which is connected to the flow restrictor tubing 54b, thereby providing a flow rate of 1.0 ml/hr. The apertures 64 and 68 in planes 15-15 and 17-17 are out of registration or alignment with ports 50a and 50c, so that no fluid flows through them, and the total flow rate through the valve is 1.0 ml/hr.

In position C, one of apertures 64 and one of apertures 66 in planes 15-15 and 16-16 are in alignment or registration with ports 50a and 50b, respectively, which are connected to restrictor tubing 54a and 54b. None of the apertures 68 in plane 17-17 is in communication with port 50c. Thus, the flow rate through the valve is the combined flow of 0.5 ml/hr and 1.0 ml/hr through ports 50a and 50b for a total flow rate of 1.5 ml/hr.

The chart in FIG. 24A may be followed in similar fashion to see that at position D, flow is only allowed through one of apertures 68 in plane 17-17, at 2.0 ml/hr. In position E, flow is allowed through apertures 64 and 68 in planes 15-15 and 17-17 (0.5 ml/hr and 2.0° ml/hr) for a combined flow rate through the valve of 2.5 ml/hr. In position F, flow is allowed through apertures 66 and 68 in planes 16-16 and 17-17 (1.0 ml/hr and 2.0 ml/hr) for a combined flow rate of 3.0 ml/hr. In position G, flow is permitted through one of the apertures 64, 66 and 68 in each of planes 15-15, 16-16 and 17-17 (0.5 ml/hr, 1.0 ml/hr and 2.0 ml/hr) for a total flow through the device of 3.5 ml/hr.

At position H and between each of the other positions, no aperture in planes 15-15, 16-16 or 17-17 is in communication with its respective port or flow restrictor tubing and there is essentially no flow through the flow control device.

Although the flow control device is illustrated in its preferred form, many variations are possible without departing from the present invention. For example, additional flow restrictors and flow streams could be provided to offer different flow rates. Also, while in the illustrated embodiment of the present invention, a fluid stream is described as entering the flow control valve through the inlet 34 and exiting through the outlet 36, it should be understood that the illustrated flow control valve is equally suitable in situations where a fluid stream enters the valve through the outlet 36 and exits the valve through the inlet 34. Therefore, as used herein, "inlet" and "outlet" are interchangeable and are used only as a naming convention. Thus, the scope of the present invention as described and claimed herein and hereafter is intended to encompass all such operable flow control valves or devices regardless of the name of the part or passage through which fluid enters or leaves the flow control valve.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A flow control valve for medical liquid comprising:
   a housing including an inlet and an outlet;
   the housing including a first cylindrical wall defining a first interior bore and first and second axially spaced-apart openings extending through the first cylindrical wall;
   a flow control member including a second cylindrical wall defining a second interior bore, the flow control member rotatably disposed within the first interior bore and having at least one discrete aperture in a first plane, at least one discrete aperture in a second plane, and a discrete aperture in a third plane;
   a first tube having a first size and communicating at one end with one of the inlet or outlet and at the other end with the first opening in the first cylindrical wall, and a second tube having a size different from the first tube and communicating at one end with the one of the inlet or outlet and at the other end with the second opening in the first cylindrical wall;
   the flow control member being rotatable between a first position and a second position, in the first position one of the at least one discrete aperture in the first plane being in communication with the first opening in the first cylindrical wall to define a first flow rate out of the discrete aperture in the third plane, and in the second position one of the at least one discrete aperture in the second plane being in communication with the second opening in the first cylindrical wall to define a second flow rate out of the discrete aperture in the third plane different from the first flow rate; and
   a cylindrical stem extending into the second interior bore defined by the second cylindrical wall of the flow control member, the cylindrical stem and the second cylindrical wall defining an cylindrical space allowing fluid communication between (i) the discrete aperture in the first plane and the discrete aperture in the third plane and (ii) the discrete aperture in the second plane and the discrete aperture in the third plane.

2. The flow control valve of claim 1, wherein (i) one of the discrete apertures in the second plane is in communication with the second opening or (ii) none of the discrete apertures in the second plane is in communication with the second opening when the flow control member is in the first position.

3. The flow control valve of claim 1, wherein fluid flow through the first and second discrete apertures of the first and second planes is combined in the cylindrical space before flowing out the discrete aperture in the third plane.

4. The flow control valve of claim 1, wherein the stem extends upwardly from a base of the housing.

5. The flow control valve of claim 1, wherein the cylindrical space enables fluid flowing through the discrete aperture in the first plane and the discrete aperture in the second plane to be summed.

6. The flow control valve of claim 1, wherein the flow control member defines at least one aperture in a fourth plane spaced between the second and third planes, the at least one aperture of the first, second and forth planes in fluid communication with the cylindrical space.

7. The flow control valve of claim 6, the first cylindrical wall defining a third axially spaced-apart opening aligned to communicate with the at least one aperture in the fourth plane.

8. The flow control valve of claim 7, the flow control member being further rotatable to a third position in which one of the at least one discrete aperture in the forth plane is in communication with the third opening in the first cylindrical wall to define a third flow rate out of the discrete aperture in the third plane.

9. The flow control valve of claim 7, which includes a third tube having a size different from the first and second tubes, the third tube communicating at one end with the inlet or outlet and at the other end with the third opening in the first cylindrical wall.

10. The flow control valve of claim 6, wherein the cylindrical space enables fluid flowing through the discrete aperture in the first plane, the discrete aperture in the second plane and the discrete aperture in the forth plane to be summed.

11. The flow control valve of claim 1, wherein the discrete aperture in a third plane communicates with an annular groove that extends at least partially around an outer circumference of the second cylindrical wall, the annular groove positioned to communicate with the other of the inlet or the outlet regardless of whether the flow control member has been rotated to the first position or the second position.

12. A flow control valve for medical liquid comprising:
   a housing (32) including an inlet (34) and an outlet (36);
   the housing (32) including a first cylindrical wall defining a first interior bore and first, second and third axially spaced-apart openings extending through the first cylindrical wall;
   a flow control member (48) including a second cylindrical wall defining a second interior bore, the flow control member (48) rotatably disposed within the first interior bore and having at least one discrete aperture in a first plane, at least one discrete aperture in a second plane, at least one discrete aperture in a third plane and a discrete aperture in a forth plane;
   a first flow restrictor communicating at one end with the inlet (34) and at the other end with the first opening in the first cylindrical wall, a second flow restrictor communicating at one end with the inlet (34) and at the other end with the second opening in the first cylindrical wall, and a third flow restrictor communicating at one end with the inlet (34) and at the other end with the third opening in the first cylindrical wall;

the flow control member (48) being rotatable between first, second and third positions, in the first position one of the at least one discrete aperture in the first plane being in communication with the first opening in the first cylindrical wall to define a first flow rate out of the discrete aperture in the fourth plane, in the second position one of the at least one discrete aperture in the second plane being in communication with the second opening in the first cylindrical wall to define a second flow rate out of the discrete aperture in the forth plane different from the first flow rate, and in the third position one of the at least one discrete aperture in the third plane being in communication with the third opening in the first cylindrical wall to define a third flow rate out of the discrete aperture in the forth plane different from the first and second flow rates; and a cylindrical stem (70) extending into the second interior bore defined by the second cylindrical wall of the flow control member (48), the cylindrical stem (70) and the second cylindrical wall defining a cylindrical space allowing fluid communication between (i) the discrete aperture in the first plane and the discrete aperture in the forth plane, (ii) the discrete aperture in the second plane and the discrete aperture in the forth plane, and (iii) the discrete aperture in the third plane and the discrete aperture in the forth plane.

13. The flow control valve of claim 12, which when in position for use, the discrete aperture in the forth plane is located elevationally below the first, second and third planes.

14. The flow control valve of claim 12, which when in position for use, the cylindrical space extends at least substantially vertically.

15. The flow control valve of claim 12, wherein at least one of the first, second and third flow restrictors is a small diameter tube.

16. The flow control valve of claim 12, wherein one of the first, second and third positions produces a combination of flows through at least two of the discrete apertures in the first, second and third planes, the combination of flows occurring in the cylindrical space.

17. The flow control valve of claim 12, wherein the discrete aperture in the forth plane communicates with an annular groove that extends at least partially around an outer circumference of the second cylindrical wall, the annular groove positioned to communicate with the outlet of the housing regardless of whether the flow control member has been rotated to the first, second or third positions.

18. A flow control valve for medical liquid comprising:

a housing including an inlet and an outlet;

the housing including a first wall defining a first interior bore and first and second axially spaced-apart openings extending through the first wall;

a flow control member including a second wall defining a second interior bore, the flow control member rotatably disposed within the first interior bore and having at least one discrete aperture in a first plane, at least one discrete aperture in a second plane, and a discrete aperture in a third plane;

a first flow restrictor communicating at one end with the inlet and at the other end with the first opening in the first wall and a second flow restrictor communicating at one end with the inlet and at the other end with the second opening in the first wall, the flow control member being rotatable between a first position and a second position, in the first position one of the at least one discrete aperture in the first plane being in communication with the first opening in the first wall to define a first flow rate out of the discrete aperture in the third plane, and in the second position one of the at least one discrete aperture in the second plane being in communication with the second opening in the first wall to define a second flow rate out of the discrete aperture in the third plane different from the first flow rate; and a stem extending into the second interior bore defined by the second wall of the flow control member, the stem and the second wall defining a space allowing fluid communication between (i) the discrete aperture in the first plane and the discrete aperture in the third plane and (ii) the discrete aperture in the second plane and the discrete aperture in the third plane.

19. The flow control valve of claim 18, wherein the stem, the second wall and the space are at least substantially cylindrical.

20. The flow control valve of claim 18, wherein the first wall of the housing is at least substantially cylindrical.

* * * * *